United States Patent
Schneider et al.

(10) Patent No.: US 10,610,923 B2
(45) Date of Patent: Apr. 7, 2020

(54) FOUNDRY MIX INCLUDING RESORCINOL

(71) Applicant: Novis Works, LLC, Canton, OH (US)

(72) Inventors: James T. Schneider, Canton, OH (US); Frances Trenta, Canton, OH (US)

(73) Assignee: Novis Works, LLC, Canton, OH (US)

( * ) Notice: Subject to any disclaimer, the term of this patent is extended or adjusted under 35 U.S.C. 154(b) by 136 days.

(21) Appl. No.: 15/875,554

(22) Filed: Jan. 19, 2018

(65) Prior Publication Data

US 2018/0207713 A1 Jul. 26, 2018

Related U.S. Application Data

(60) Provisional application No. 62/449,157, filed on Jan. 23, 2017.

(51) Int. Cl.
| | |
|---|---|
| *C08L 63/00* | (2006.01) |
| *B22C 1/22* | (2006.01) |
| *C07C 39/10* | (2006.01) |
| *C08L 63/04* | (2006.01) |
| *B22C 1/20* | (2006.01) |
| *B22C 7/00* | (2006.01) |

(52) U.S. Cl.
CPC .............. *B22C 1/226* (2013.01); *B22C 1/205* (2013.01); *B22C 1/222* (2013.01); *B22C 1/2253* (2013.01); *B22C 7/00* (2013.01); *C07C 39/10* (2013.01); *C08L 63/00* (2013.01); *C08L 63/04* (2013.01); *C08L 2205/05* (2013.01)

(58) Field of Classification Search
CPC .......... C07C 39/10; C08L 63/00; C08L 63/04; C08L 2205/05; B22C 1/226; B22C 1/205; B22C 1/222; B22C 7/00
USPC ....................................................... 523/145
See application file for complete search history.

(56) References Cited

U.S. PATENT DOCUMENTS

| | | |
|---|---|---|
| 4,469,517 A | 9/1984 | Cooke, Jr. |
| 4,600,733 A | 7/1986 | Ohashi et al. |
| 5,043,412 A | 8/1991 | Chandramouli et al. |
| 5,639,806 A | 6/1997 | Johnson et al. |
| 5,916,933 A | 6/1999 | Johnson et al. |
| 6,604,567 B1 | 8/2003 | Woodson et al. |
| 6,662,854 B2 | 12/2003 | Woodson et al. |
| 6,684,936 B2 | 2/2004 | Woodson et al. |
| 6,686,402 B2 | 2/2004 | Woodson et al. |
| 7,723,401 B2 | 5/2010 | Wang et al. |
| 2003/0055125 A1* | 3/2003 | Hutchings ................. B22C 1/20 523/139 |
| 2011/0073267 A1* | 3/2011 | Kloskowski .............. B22C 3/00 164/14 |

FOREIGN PATENT DOCUMENTS

| | | |
|---|---|---|
| DE | 3018466 | 11/1980 |
| DE | 68914969 | 12/1994 |
| DE | 68918057 | 2/1995 |
| EP | 0153714 | 9/1985 |
| EP | 0735234 | 10/1996 |

* cited by examiner

*Primary Examiner* — Hannah J Pak

(74) *Attorney, Agent, or Firm* — Sand, Sebolt & Wernow Co., LPA

(57) ABSTRACT

A foundry mix includes a major amount of a foundry aggregate and an effective binding amount of a binder system. The binder system cures in the presence of sulfur dioxide and a free radical initiator. The binder system may include (1) 10 to 70 parts by weight of an epoxy novolac resin; (2) 0.5 to 10 parts by weight of resorcinol; (3) 20 to 70 parts by weight of a monomeric or polymeric acrylate; and (4) an effective amount of a free radical initiator. Notably, (1), (2), (3) and (4) are separate components or mixed with another of said components, provided (4) is not mixed with (3), where said parts by weight are based upon 100 parts of the binder system.

11 Claims, 3 Drawing Sheets

200

202
fabricating a foundry shape by introducing a foundry mix into a pattern to form the foundry shape, and curing said shape with gaseous sulfur dioxide 204
pouring said metal while in the liquid state into said foundry shape 206
allowing said metal to cool and solidify 208
separating the cast article

FIG.2

FOUNDRY MIX INCLUDING RESORCINOL

CROSS REFERENCE TO RELATED APPLICATIONS

This application claims the benefit of U.S. Provisional Application Ser. No. 62/449,157, filed on Jan. 23, 2017; the disclosure of which is incorporated herein by reference.

BACKGROUND

Technical Field

The present disclosure relates generally to foundry binder systems, which will cure in the presence of sulfur dioxide and a free radical initiator, comprising (a) an epoxy novolac resin; (b) preferably a bisphenol F epoxy resin alone or bisphenol F epoxy resin with a slight amount of bisphenol A epoxy resin; (c) an acrylate; (d) resorcinol or other polyhydroxy benzenes; and (e) an effective amount of a free radical initiator. The foundry binder systems are used for making foundry mixes. The foundry mixes are used to make foundry shapes (such as cores and molds) which are used to make metal castings.

Background Information

Foundry binder systems, which cure in the presence of a free radical initiator, are known in the art. For instance, U.S. Pat. Nos. 6,604,567; 6,662,854; 6,684,936; 6,686,402; and 7,723,401 disclose foundry core mold systems that include an epoxy resins that cure in the presence of a free radical initiator.

In order for the epoxy resins to be useful in these situations, the epoxy resin must be used in conjunction with an acrylic monomer or polymer, typically trimethylolpropane triacrylate (TMPTA) however other acrylates are entirely possible.

Typically, these binders are packaged in two parts. One part ("Part One") is a mixture of a resins (such as bisphenol A epoxy resin or bisphenol-F epoxy resin) and cumene hydroperoxide (the free radical initiator). The other part ("Part Two") is a mixture of one or more resins, a multifunctional acrylate, and other optional components. The multifunctional acrylate is typically trimethylolpropane triacrylate (TMPTA).

Part One and Part Two of the binder are mixed with a foundry aggregate, typically sand, to form a foundry mix. The total amount of binder used to form the foundry mix. The foundry mix may be blown or compacted into a pattern where it is gassed with sulfur dioxide (SO2) to produce a cured core or mold. Thereafter, molten metal is poured into the cured core/mold and allowed to form a desired shape, such as an engine block, amongst many other shapes.

SUMMARY

While these prior art foundry binder systems (i.e., U.S. Pat. Nos. 6,604,567; 6,662,854; 6,684,936; 6,686,402; and 7,723,401) may be beneficial for specific applications, they are not without drawbacks. For example, a need continues to exist for foundry binder systems that utilize more acrylate, which could lead to additional benefits. Moreover, the inventors have determined that the "other optional components" may significantly affect the performance of the foundry binder systems. The present disclosure addresses these and other issue. The present disclosure addresses these issues by providing a foundry mix that includes resorcinol which has, upon information and belief, heretofore never been utilized in foundry mixes.

In one particular embodiment of the present disclosure, a foundry binder system may provide 20 to 70 weight percent of epoxy novolac resin, preferably from 35 to 60 weight percent; 10 to 25 weight percent of free radical initiator, preferably from 15 to 20 weight percent; and 20 to 35 weight percent of multifunctional acrylate, preferably from 25 to 32 weight percent, where the weight percent is based upon 100 parts of the binder system.

In one particular example, an embodiment of the present disclosure may provide a foundry binder system utilizing sand, a Part One mix, and a Part Two mix of the foundry binder system. Part One includes Bisphenol F epoxy resin at 70% (parts by weight) and cumene hydroperoxide (TRIGONOX K-90) at 30% (parts by weight). Part Two includes epoxy novolac resin at 31% (parts by weight), resorcinol at 3.8% (parts by weight), dibasic ester at 7.6% (parts by weight), an acrylate at 56.40% (parts by weight), and silane at 1.2% (parts by weight).

In another particular example, an embodiment of the present disclosure may provide a foundry binder system utilizing sand, Part One, and Part Two of the foundry binder system. Part One includes Bisphenol F epoxy resin at 69% (parts by weight), Bisphenol A epoxy resin at 1% (parts by weight), and cumene hydroperoxide (TRIGONOX K-90) at 30% (parts by weight). Part Two includes epoxy novolac resin at 31% (parts by weight), resorcinol at 3.8% (parts by weight), dibasic ester at 7.6% (parts by weight), an acrylate at 56.40% (parts by weight), silane at 1.2% (parts by weight).

In another particular example, an embodiment of the present disclosure may provide a foundry binder system utilizing sand, Part One, and Part Two of the foundry binder system. Part One includes Bisphenol F epoxy resin at 68% (parts by weight), Bisphenol A epoxy resin at 2% (parts by weight), and cumene hydroperoxide (TRIGONOX K-90) at 30% (parts by weight). Part Two includes epoxy novolac resin at 31% (parts by weight), resorcinol at 3.8% (parts by weight), dibasic ester at 7.6% (parts by weight), an acrylate at 56.40% (parts by weight), silane at 1.2% (parts by weight).

In another particular example, an embodiment of the present disclosure may provide a method for preparing a foundry shape comprising: (a) introducing a foundry mix into a pattern to form a foundry shape; and (b) curing said shape with gaseous sulfur dioxide; wherein said foundry mix comprises: (c) 70 to 99 parts by weight of a foundry aggregate, and a foundry binder comprising: (d) 20 to 70 parts by weight of an epoxy novolac resin; (e) 20 to 35 parts by weight of a multifunctional acrylate; (f) 0.5 to 10 parts by weight of resorcinol; (g) 10 to 25 parts by weight of amount of a free radical initiator, provided (d) is not mixed with (g), and where said parts by weight are based upon 100 parts of binder.

In another particular example, an embodiment of the present disclosure may provide a foundry binder system including: an aggregate; a first portion (Part One), wherein Part One includes an epoxy resin in a range from 25 to 70 parts by weight, and cumene hydroperoxide in a range from 10 to 40 parts by weight; a second portion (Part Two), wherein Part Two includes an epoxy novolac resin in a range from 10 to 40 parts by weight, resorcinol in a range from 0.5 to 10 parts by weight, dibasic ester in a range from 2 to 10 parts by weight, an acrylate in a range from 20 to 70 parts by weight, and silane in a range from 0.2 to 5 parts by weight; and wherein the aggregate, Part One, and Part Two are mixed together and exposed to sulfur dioxide to cure the aggregate into a foundry mold.

In yet another aspect, one exemplary embodiment of the present disclosure may provide a process for preparing a foundry shape comprising: introducing a foundry mix into a pattern to form a foundry shape; and curing said shape with gaseous sulfur dioxide; wherein said foundry mix comprises: (a) from 70 to 99 parts by weight of a foundry aggregate, and a foundry binder comprising: (b) 20 to 70 parts by weight of an epoxy novolac resin; (c) 20 to 35 parts by weight of a multifunctional acrylate; (d) 0.5 to 10 parts by weight of resorcinol; (e) an effective amount of amount of a free radical initiator, provided (b) is not mixed with (e), and where said parts by weight are based upon 100 parts of binder.

In yet another aspect, one exemplary embodiment of the present disclosure may provide a method of casting a metal article comprising: fabricating a foundry shape by introducing a foundry mix into a pattern to form the foundry shape, and curing said shape with gaseous sulfur dioxide; wherein said foundry mix comprises: (a) from 70 to 99 parts by weight of a foundry aggregate, and a foundry binder comprising: (b) 20 to 70 parts by weight of an epoxy novolac resin; (c) 20 to 35 parts by weight of a multifunctional acrylate; (d) 0.5 to 10 parts by weight of resorcinol; (e) an effective of amount of a free radical initiator, provided (b) is not mixed with (e), and where said parts by weight are based upon 100 parts of binder; pouring said metal while in the liquid state into said foundry shape; allowing said metal to cool and solidify; and separating the cast article.

BRIEF DESCRIPTION OF THE SEVERAL VIEWS OF THE DRAWINGS

A sample embodiment of the disclosure is set forth in the following description, is shown in the drawings and is particularly and distinctly pointed out and set forth in the appended claims. The accompanying drawings, which are fully incorporated herein and constitute a part of the specification, illustrate various examples, methods, and other example embodiments of various aspects of the disclosure. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

FIG. 2 is a flowchart representing an exemplary method of casting a metal article.

Similar numbers refer to similar parts throughout the drawings.

DETAILED DESCRIPTION

Figure 1:
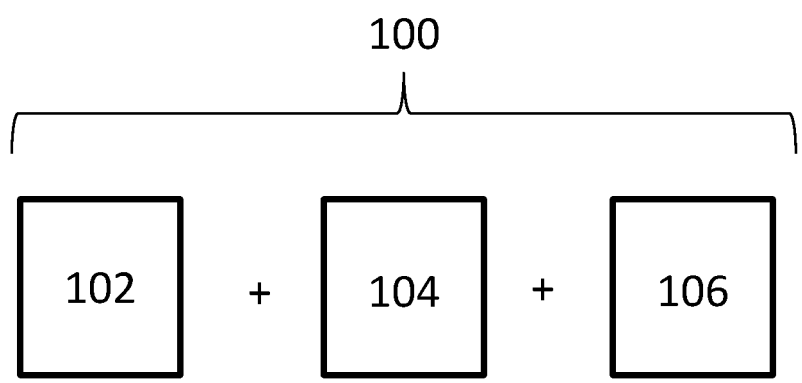
FIG. 1 is a diagram representing a foundry binder system including an aggregate, a first portion (Part One), and a second portion (Part Two), wherein the aggregate, Part One, and Part Two are mixed together and exposed to sulfur dioxide to cure the aggregate into a foundry mold.

The present disclosure provides a system that provides specific utility for sandcasting molds that are used are used for forming molten metal. As depicted in FIG. 1, the chemical system 100 includes a first portion (i.e., Part One) 102 and a second portion (i.e., Part Two) 104 that are stored separately and then mixed together with foundry aggregate 106 (i.e., sand). Collectively, the chemical system 100 includes a major amount of a foundry aggregate 106, an effective binding amount of a binder system, which will cure in the presence of sulfur dioxide and a free radical initiator, comprising 20 to 40 parts by weight of an epoxy novolac resin; 40 to 60 parts by weight of a monomeric or polymeric acrylate; 1 to 5 parts by weight of resorcinol, and an effective amount of a free radical initiator.

Bisphenol F epoxy resin, and possibly a small amount of Bisphenol A epoxy resin, and cumene hydroperoxide (the free radical initiator) collectively define Part One 102 and are first stored independently in the first portion. Epoxy novolac resin, resorcinol, a dibasic ester, and an acrylate, and in one particular embodiment, collectively define Part Two 104 and are stored independently in the second portion. Then, the first and second portions are mixed with the foundry aggregate and exposed to sulfur dioxide which effects curing of the chemical system to form a foundry mold. Notably, Part Two 104 may include additional substances, or may have fewer substances, however in accordance with the present disclosure, Part Two 104 ordinarily includes resorcinol.

The following description provides more information on the above referenced portions of Part One 102 of the foundry binder system and Part Two 104 of the foundry binder system 100 in accordance with the present disclosure.

Part One of the Foundry Binder System

Part One 102 of the system 100 may use of epoxy novolacs as the SO2 cured binder, instead of epoxy resins based on bisphenol A epoxy resin or bisphenol F epoxy resin alone. In one particular embodiment, this may improve the hot strength of cores and molds made with the binder, so that the cores and molds hold up better during microwave and conventional oven drying operations. The magnitude of the improvement in performance, as measured by tensile strength is identified hereinafter. Cores and molds made from the binders described in this invention are much more rigid at typical oven curing temperatures and resist distortion and cracking. Furthermore, the cores can be handled sooner because the cool-down time required is not as long, which increases productivity.

While the epoxy resin of Part One 102 is Bisphenol F epoxy resin (with the possibility of a small amount of Bisphenol A epoxy resin, such as 1 part by weight or 2 parts by weight or 3 parts by weight), another epoxy resin is entirely possible, such that the resin have one or more epoxide groups, i.e.,

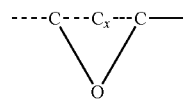

wherein x is zero or a whole number, typically from 1 to 4. Other potential epoxy resins typically used in foundry applications are diglycidyl ethers of bisphenol A, which is a monomer. These are made by reacting epichlorohydrin with the monomer bisphenol A in the presence of an alkaline catalyst. By controlling the operating conditions and varying the ratio of epichlorohydrin to bisphenol A, products of different molecular weight can be made. Other commonly used epoxy resins include the diglycidyl ethers of other bisphenol compounds such as bisphenol B, F, G and H, each of which are monomers. Epoxy resins of the type described above based on various bisphenols are available from a wide variety of commercial sources. Monomers such as bisphenol F have a chemical composition generally depicted as follows:

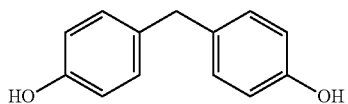 [SMILES: Oc1ccc(Cc2ccc(O)cc2)cc1]

Epoxy resins such as bisphenol F epoxy resin have a different chemical composition than monomer compounds. Specifically, bisphenol F epoxy resin has a chemical composition generally depicted as follows:

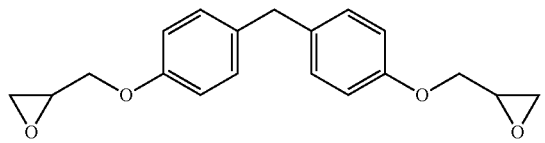 [SMILES: c1cc(OCC2CO2)ccc1Cc1ccc(OCC2CO2)cc1]

The epoxy novolac resin component of the present disclosure, however, comprises an "epoxy novolac resin". Epoxy novolac resins are less commonly known and used than other epoxy resins. Epoxy novolac resins are typically prepared by reacting an epihalohydrin, e.g. epichlorohydrin, with the resinous condensate of an aldehyde, e.g. formaldehyde, and either a monohydric phenol, e.g. phenol itself, or a polyhydric phenol, preferably in the presence of a basic catalyst, e.g. sodium or potassium hydroxide, by methods well known in the art. Examples of epoxy novolac resins include epoxy cresol and epoxy phenol novolacs, which are produced by reacting a novolac resin (usually formed by the reaction of orthocresol or phenol and formaldehyde) with epichlorohydrin, 4-chloro-1,2-epoxybutane, 5-bromo-1,2-epoxypentane, 6-chloro-1,3-epoxyhexane and the like.

The epoxy novolac resin, or blends of epoxy novolac resins, used in the binders, typically have an average epoxide functionality of at least 2.2 to 3.5, preferably from about 2.3 to about 3.0. Particularly preferred are epoxy novolacs having an average weight per epoxy group of 165 to 200. Although the viscosities of the epoxy novolac resins are high, usually greater than 5,000 cps at 25° C., the epoxy component viscosity is reduced to a workable level when the epoxy novolac resin is mixed with the free radical initiator and/or solvent.

The foundry binder system 100 of the present disclosure preferably contains some bisphenol F epoxy resin in an amount (typically from 60 to 80 parts by weight based on 100 parts of binder, and in one particular example about 70 parts by weight), which is useful in reducing the viscosity of the epoxy novolac resin, but does not significantly affect the other required properties of the binders or cores made with the binder. The binder preferably contains sufficient bisphenol F epoxy resin to obtain a binder (or the parts of the binder if the binder is formulated as more than one part), with a viscosity less than 2000 centipoise at room temperature, preferably less than 1500 centipoise, and most preferably less than 900 centipoise.

Although not necessarily preferred, other epoxy resins, such as bisphenol A epoxy resin, may also be added to the binder to lower the costs of the binder. In one exemplary embodiment, not more than 10 parts by weight (i.e., weight percent) of these other epoxy resins and monomeric bisphenol A are typically used, where the weight percent is based upon the weight percent of the epoxy novolac resin in the binder system. Other epoxy resins, such as bisphenol A epoxy resin and bisphenol F epoxy resin, and monomeric bisphenol compounds, such as bisphenol A, may be added to the binder.

Examples of other epoxy resins include halogen-substituted aliphatic epoxides and diglycidyl ethers of other bisphenol compounds such as bisphenol B, F, G, and H epoxy resins. Examples of halogen-substituted aliphatic epoxides include epichlorohydrin, 4-chloro-1,2-epoxybutane, 5-bromo-1,2-epoxypentane, 6-chloro-1,3-epoxyhexane and the like. The most widely used epoxy resins are diglycidyl ethers of bisphenol A.

The free radical initiator is a peroxide and/or hydroperoxide. Examples include ketone peroxides, peroxy ester free radical initiators, alkyl oxides, chlorates, perchlorates, and perbenzoates. Preferably, however, the free radical initiator is a hydroperoxide or a mixture of peroxide and hydroperoxide. Hydroperoxides particularly preferred in the invention include t-butyl hydroperoxide, cumene hydroperoxide, paramenthane hydroperoxide, etc. The organic peroxides may be aromatic or alkyl peroxides. Examples of useful diacyl peroxides include benzoyl peroxide, lauroyl peroxide and decanoyl peroxide. Examples of alkyl peroxides include dicumyl peroxide and di-t-butyl peroxide.

Cumene hydroperoxide and/or a multifunctional acrylate, such as trimethylolpropane triacrylate, may added to the epoxy novolac resin before mixing it with the foundry aggregate. Optionally, a solvent or solvents may be added to reduce system viscosity or impart other properties to the binder system such as humidity resistance. Examples of solvents include aromatic hydrocarbon solvents, such as such as o-cresol, benzene, toluene, xylene, ethylbenzene, and naphthalenes; reactive epoxide diluents, such as glycidyl ether; or an ester solvent, such as dioctyl adipate, rapeseed methyl ester, and the like, or mixtures thereof. If a solvent is used, sufficient solvent should be used so that the resulting viscosity of the epoxy resin component is less than 1,000 centipoise, preferably less than 400 centipoise. Generally, however, the total amount of solvent is used in an amount of 0 to 25 weight percent based upon the total weight of the epoxy resin.

Part Two of the Foundry Binder System

Part Two 104 of the foundry binder system includes the reactive unsaturated acrylic monomer, polymer, or mixture thereof contains ethylenically unsaturated bonds. Examples of such materials include a multifunctional acrylate, such as trimethylolpropane triacrylate (TMPTA) or any other variety of monofunctional, difunctional, trifunctional, tetrafunctional and pentafunctional monomeric acrylates and methacrylates. A representative listing of these monomers includes alkyl acrylates, acrylated epoxy resins, cyanoalkyl acrylates, alkyl methacrylates, cyanoalkyl methacrylates, and difunctional monomeric acrylates. Other acrylates, which can be used, include trimethylolpropane triacrylate, methacrylic acid and 2-ethylhexyl methacrylate. Typical reactive unsaturated acrylic polymers, which may also be used include epoxy acrylate reaction products, polyester/urethane/acrylate reaction products, acrylated urethane oligomers, polyether acrylates, polyester acrylates, and acrylated epoxy resins.

Part Two 104 of the foundry binder system 100 of the present disclosure further includes a phenolic substance, such as a polyhydroxy benzene, preferably a di-hydroxy and tri-hydroxy benzene, still more preferably resorcinol (1,3-dihydroxy benzene). Some other exemplary non-limiting suitable examples of the resorcinol compound include non-functionalized resorcinol compounds such as resorcinol; and functionalized resorcinol compounds such as orcinol, 2-methylresorcinol, phloroglucinol, 1,2,4-benzenetriol, pyrogallol, 3,5-dihydroxybenzaldehyde, 2,4-dihydroxybenzaldehyde, 4-ethylresorcinol, 2,5-dimethylresorcinol, 5-methylbenzene-1,2,3-triol, 3,5-dihydroxybenzyl alcohol, 2,4,6-trihydroxytoluene, 4-chlororesorcinol, 2',6'-dihydroxyacetophenone, 2',4'-dihydroxyacetophenone, 3',5'-dihydroxyacetophenone, 2,4,5-trihydroxybenzaldehyde, 2,3,4-trihydroxybenzaldehyde, 2,4,6-trihydroxybenzaldehyde, 3,5-dihydroxybenzoic acid, 2,4-dihydroxybenzoic acid, 2,6-dihydroxybenzoic acid, 1,3-dihydroxynaphthalene, 2',4'-dihydroxypropiophenone, 2',4'-dihydroxy-6'-methylacetophenone, 1-(2,6-dihydroxy-3-methylphenyl)ethanone, 3-methyl 3,5-dihydroxybenzoate, methyl 2,4-dihydroxybenzoate, gallacetophenone, 2,4-dihydroxy-3-methylbenzoic acid, 2,6-dihydroxy-4-methylbenzoic acid, methyl 2,6-dihydroxybenzoate, 2-methyl-4-nitroresorcinol, 2,4,5-trihydroxybenzoic acid, 3,4,5-trihydroxybenzoic acid, 2,3,4-trihydroxybenzoic acid, 2,4,6-trihydroxybenzoic acid, 2-nitrophloroglucinol or a combination thereof. In some embodiments, the resorcinol compound is resorcinol, orcinol, 2-methylresorcinol, phloroglucinol, 1,2,4-benzenetriol, pyrogallol, 3,5-dihydroxybenzaldehyde, 2,4-dihydroxybenzaldehyde, 4-ethylresorcinol, 4-chlororesorcinol or a combination thereof.

In accordance with a non-limiting example of the present disclosure, the use of the polyhydroxy benzene, preferably a di-hydroxy and tri-hydroxy benzene, still more preferably resorcinol (1,3-dihydroxy benzene) in Part Two 104 of system 100 provides some advantages to the binder. For example, some advantages of the polyhydroxy benzene enable the resin to have a higher thermal stability (improves hot-strength); enables the resin to establish an increase in front-end tensile strength (early tensile strength is higher for improved handling of cores); and the humidity resistance is improved.

Part Two 104 of the foundry binder system 100 further includes A-187 silane, or another epoxy functional silanes which may be suitable for use as adhesion promoters in, urethane, epoxy, polysulfide, silicone, and acrylic caulks, coatings, sealants and adhesives. The silane may provide enhanced electrical properties of epoxy based electronic encapsulant and packaging materials, resulting from improved bonding between resin and substrate or filler. The silane provides itself useful for the quartz (in the sand aggregate) filled epoxy encapsulants, pre-mix formulations, sand-filled epoxy concrete patching materials, and metal filled epoxy materials suitable for mold die tools. Some exemplary silanes aside from A187 silane include but are not limited to mixtures of methyltrimethoxysilane and propyltrimethoxysilane, of propyltrimethoxysilane and vinyltrimethoxysilane or phenyltrimethoxysilane and propyltrimethoxysilane, and of phenyltriethoxysilane and propyltriethoxysilane, to name but a few examples. Other useful silanes may include aminoalkyl-functional alkoxysilane which carries in particular an aminoalkyl group from the series consisting of aminoethylaminopropyl, aminoethylaminoethylaminopropyl, N-methylaminopropyl, N-(n-butyl)aminopropyl, N-cyclohexylaminopropyl, and N-phenylaminopropyl, and at least one alkoxy group from the series consisting of methoxy, ethoxy, and propoxy. Examples of such are 3-aminopropyltrialkoxysilanes, such as 3-aminopropyltrimethoxysilane, 3-aminopropyltriethoxysilane, N-aminoethyl-3-aminopropyltrialkoxysilanes, N-aminoethyl-N-aminoethyl-3-aminopropyltrialkoxysilanes, N-methyl-aminopropyltrialkoxysilanes, N-n-butyl-aminopropyltrialkoxysilanes, N-cyclohexyl-aminopropyltrialkoxysilanes, N-phenyl-aminopropyltrialkoxysilanes, 3-aminopropyl-methyldialkoxysilanes, N-aminoethyl-3-aminopropyl-methyldialkoxysilanes, N-aminoethyl-N-aminoethyl-3-aminopropyl-methyldialkoxysilanes, N-methyl-aminopropyl-methyldialkoxysilanes, N-n-butyl-aminopropyl-methyldialkoxysilanes, N-cyclohexyl-aminopropyl-methyldialkoxysilanes, and N-phenyl-aminopropyl-methyl.

It will be apparent to those skilled in the art that other additives such as other silanes, silicones, benchlife extenders, release agents, defoamers, wetting agents, etc. can be added to the aggregate, or foundry mix. The particular additives chosen will depend upon the specific purposes of the formulator.

Mixing Part One and Part Two with Aggregate

Various types of aggregates 106 and amounts of binder are used to prepare foundry mixes by methods well known in the art. Ordinary shapes, shapes for precision casting, and refractory shapes can be prepared by using the binder systems and proper aggregate. The amount of binder and the type of aggregate used are known to those skilled in the art. The preferred aggregate 106 employed for preparing foundry mixes is sand wherein at least about 70 weight percent, and preferably at least about 85 weight percent, of the sand is silica. Other suitable aggregate materials for ordinary foundry shapes include zircon, olivine, aluminosilicate, chromite sands, and the like.

In ordinary sand type foundry applications, the amount of binder is generally no greater than about 10% by weight and frequently within the range of about 0.5% to about 7% by weight based upon the weight of the aggregate. Most often, the binder content for ordinary sand foundry shapes ranges from about 0.6% to about 5% by weight based upon the weight of the aggregate in ordinary sand-type foundry shapes.

The foundry mix is molded into the desired shape by ramming, blowing, or other known foundry core and mold making methods. The shape is then cured almost instantaneously by the cold-box process, using vaporous sulfur dioxide as the curing agent (most typically a blend of nitrogen, as a carrier, and sulfur dioxide containing from 35 weight percent to 65 weight percent sulfur dioxide), described in U.S. Pat. Nos. 4,526,219 and 4,518,723, amongst others, which are hereby incorporated by reference. The shaped article is preferably exposed to effective catalytic amounts of 100 percent vaporous sulfur dioxide, although minor amounts of a carrier gas may also be used. The exposure time of the sand mix to the gas is typically from 0.5 to 3 seconds. Although the foundry shape is cured after gassing with sulfur dioxide, oven drying may be required if the foundry shape is coated with a water based refractory coating.

Typically, the amounts of the components used in the binder system are from 20 to 70 weight percent of epoxy novolac resin, preferably from 35 to 60 weight percent; 10 to 25 weight percent of free radical initiator, preferably from 15 to 20 weight percent; and 20 to 35 weight percent of multifunctional acrylate, preferably from 25 to 32 weight percent, where the weight percent is based upon 100 parts of the binder system.

The core and/or mold may be formed into an assembly. When making castings, the assembly is typically coated with a water-based refractory coating and passed through a conventional or microwave oven to remove the water from the coating. The item is then ready to be handled for further processing. In one particular embodiment, the process for preparing a foundry shape includes introducing a foundry mix into a pattern to form a foundry shape; and curing said shape with gaseous sulfur dioxide.

In accordance with one aspect of the present disclosure, the shape cured core is formed into the shape of a negative engine block. This allows molten metal, such as Aluminum, or an aluminum-based alloy, to be poured into the mold. The metal is allowed to cool and cure so as to form an engine block or other desired shaped.

In operation, a method of casting a metal article may include fabricating a foundry shape by introducing a foundry mix into a pattern to form the foundry shape, and curing said shape with gaseous sulfur dioxide; pouring said metal while in the liquid state into said foundry shape, which could be shaped as a negative engine block; allowing said metal to cool and solidify; and then separating the cast article, such as the engine block. In some instances, the cast article (i.e., the engine block) can be shaken to release the foundry aggregate from the cooled, cured, and cast metal article.

FIG. 2 depicts an exemplary method of casting a metal article generally at 200. The method 200 may include fabricating a foundry shape by introducing a foundry mix into a pattern to form the foundry shape, and curing said shape with gaseous sulfur dioxide, which is shown generally at 202. In one non-limiting example, the foundry mix includes: (a) 20 to 70 parts by weight of an epoxy novolac resin; (b) 20 to 65 parts by weight of a multifunctional acrylate; (c) 0.5 to 10 parts by weight of resorcinol; (d) an effective of amount of a free radical initiator, provided (a) is not mixed with (d) prior to mixing the foundry mix, and where said parts by weight are based upon 100 parts of the foundry mix. The method 200 may further include pouring said metal while in the liquid state into said foundry shape, which is shown generally at 204. The method 200 may further include allowing said metal to cool and solidify, which is shown generally at 206. The method 200 may further include separating the cast article, which is shown generally at 208. In one example, method 200 may further provide wherein the foundry mix includes at least 1 parts by weight of bisphenol A epoxy resin. In this or another example, method 200 may further provide wherein the foundry mix further includes (e) a dibasic ester in a range from 2 to 10 parts by weight. In this or another example, method 200 may further provide wherein the binder system further includes (6) a silane in a range from 0.5 to 2 parts by weight. In this or another example, method 200 may further provide wherein the resorcinol is about 3.8 parts by weight.

Figure 3:
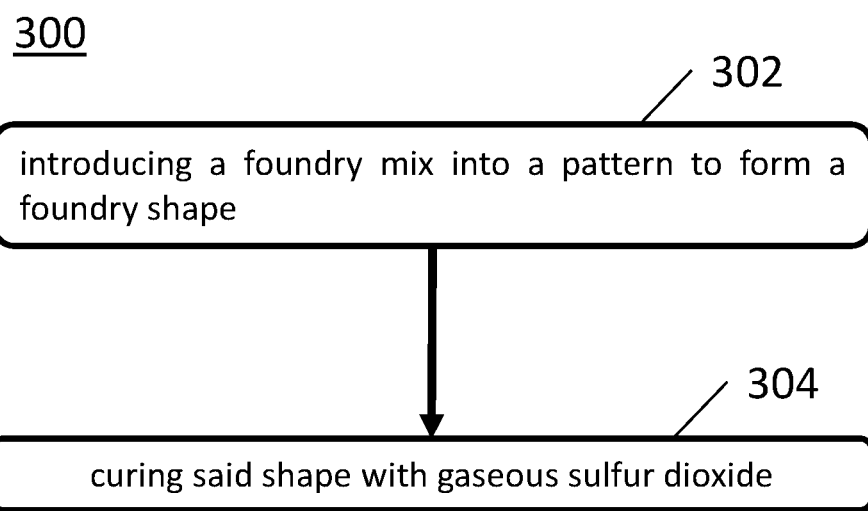
FIG. 3 is a flowchart representing an exemplary method of preparing a foundry shape.

FIG. 3 depicts an exemplary method or process for preparing a foundry shape generally at 300. Method 300 may include introducing a foundry mix into a pattern to form a foundry shape, which is shown generally at 302. Method 300 may include curing said shape with gaseous sulfur dioxide, which is shown generally at 304. In one particular embodiment of method 300 said foundry mix comprises: (a) from 70 to 99 parts by weight of a foundry aggregate, and a foundry binder comprising: (b) 20 to 70 parts by weight of an epoxy novolac resin; (c) 20 to 35 parts by weight of a multifunctional acrylate; (d) 0.5 to 10 parts by weight of resorcinol, however other parts by weight are possible, such as 3.8 parts by weight; (e) an effective amount of a free radical initiator, provided (b) is not mixed with (e), and where said parts by weight are based upon 100 parts of binder.

Example Tensile Tests

The numbered examples are examples that illustrate the practice of the present disclosure. All parts are by weight, unless otherwise indicated.

The tensile strength of "dog bones" formed from the Part One 102 and Part Two 104 portions of the present disclosure is used to determine differences in tensile strength when subjected to a tensile force. The tensile tester used in each of the following examples consists of a dog bone-shaped samples formed from the Part One 102 and Part Two 104 portions of the present disclosure and cured in the presence of SO2. The tensile tester is a Thwing-Albert QC-3A.

Dog Bone Preparation for Tensile Strength Test Procedure

In a Hobart mixing bowl N-50 (Serial No. 31-1402-254) using speed 1 with stainless steel paddle, 4000 grams of standard sand at 72° F. are mixed with 1.20% of the binder (epoxy resin and additives pre-blended with the TMPTA) based on sand. Example 1 utilizes Badger FW-55 sand and Example 2 utilizes Wedron 430 sand. The Part One/Part Two ratio is 50:50 (i.e., 1:1). Part One mass is 24 grams and Part Two mass is 24 grams. This mixture is mixed at speed #1 for two minutes. After two minutes, sand mix is flipped several times to blend any dry sand at the bottom of the bowl into the sand-binder mix. Then the mixture is mixed for another two minutes, for a total of 4 minutes.

The sand-binder mix is placed in a "dog bone" form, where it is gassed for 12 seconds with 100% anhydrous SO2 (at 30 PSI) and after a 3 second dwell time, the dog bone is purged with N2 for thirty seconds (at 35 PSI). The SO2 gas line temperature is 225° F. and the N2 gas line temperature is 225° F.

After purging the dog bone, the dog bone is connected to a tensile strength tester. The tensile tester is a Thwing-Albert QC-3A (Serial No. 62229). The tensile strength conditions provide the tensile tester moving at a speed of 2 inch/min until contacting the dog bone, then once contact is established the speed drops to 0.2 inch/min.

Part One and Part Two are mixed with the sand and cured into a dog bone in the method described above and tested by the tensile tester. The tensile strength tester tested the dog bone tensile strength at different time intervals after curing. The first time interval was after 2 minutes from curing (at about 30% relative humidity (RH)), the second time interval was 2 hours from curing (at about 30% RH), the third time interval was 24 hours from curing (at 30% RH), and the fourth time interval was 24 hours from curing (at about 75% RH). Each ambient temperature was about 73° F. For each time interval, three tensile strength results were obtained (in psi) and averaged.

Example One

Example One utilizes sand (Badger FW-55), Part One, and Part Two of the foundry binder system. Part One includes Bisphenol F epoxy resin (DER 354; lot D344F4G036) at 70% (parts by weight) and cumene hydroperoxide (TRIGONOX K-90) at 30% (parts by weight). Part Two includes epoxy novolac resin (DEN 431; lot D344F79940) at 31% (parts by weight), resorcinol at 3.8% (parts by weight), dibasic ester (DBE) at 7.6%, an acrylate (SR 352H TMPTA) at 56.40% (parts by weight), silane (A187) at 1.2%.

After two minutes from curing at about 30% RH, the three tensile strength test results of the Example One dog bone sample were 217.0, 194.3, and 187.8, for an average of 199.7 psi. After two hours from curing at about 30% RH, the three tensile strength test results were 251.8, 237.5, and 225.9, for an average of 238.4 psi. After 24 hours from curing at about 30% RH, the three tensile strength test results were 248.6, 270.1, and 274.6, for an average of 264.4 psi. After 24 hours from curing at about 75% RH, the three tensile strength test results were 138.2, 137.6, and 128.6, for an average of 134.8 psi.

Example Two

Example Two utilizes sand (Badger FW-55), Part One, and Part Two of the foundry binder system. Part One includes Bisphenol F epoxy resin (DER 354; lot D344F4G036) at 70% (parts by weight) and cumene hydroperoxide (TRIGONOX K-90) at 30% (parts by weight). Part Two includes epoxy novolac resin (DEN 431; lot D344F79940) at 31% (parts by weight), resorcinol at 3.8% (parts by weight), dibasic ester (DBE) at 7.6%, an acrylate (SR 295 acrylic) at 56.40% (parts by weight), silane (A187) at 1.2%.

After two minutes from curing at about 30% RH, the three tensile strength test results of the Example Two dog bone sample were 220.1, 203.4, and 189.6, for an average of 204.4 psi. After two hours from curing at about 30% RH, the three tensile strength test results were 250.0, 242.1, and 241.7, for an average of 244.6 psi. After 24 hours from curing at about 30% RH, the three tensile strength test results were 270.3, 264.9, and 267.0, for an average of 267.4 psi. After 24 hours from curing at about 75% RH, the three tensile strength test results were 155.3, 172.4, and 159.6, for an average of 162.4 psi.

Example Three

Example Three utilizes sand (Wedron 430), Part One, and Part Two of the foundry binder system. Part One includes Bisphenol F epoxy resin (DER 354; lot D344F4G036) at 70% (parts by weight) and cumene hydroperoxide (TRIGONOX K-90) at 30% (parts by weight). Part Two includes epoxy novolac resin (DEN 431; lot D344F79940) at 31% (parts by weight), resorcinol at 3.8% (parts by weight), dibasic ester (DBE) at 7.6%, an acrylate (SR 351H TMPTA) at 56.40% (parts by weight), silane (A187) at 1.2%.

After two minutes from curing at about 30% RH, the three tensile strength test results of the Example Three dog bone sample were 197.3, 164.5, and 144.1, for an average of 168.6 psi. After two hours from curing at about 30% RH, the three tensile strength test results were 231.4, 216.8, and 199.6, for an average of 215.9 psi. After 24 hours from curing at about 30% RH, the three tensile strength test results were 252.7, 231.1, and 249.3, for an average of 244.4 psi. After 24 hours from curing at about 75% RH, the three tensile strength test results were 131.0, 123.0, and 105.2, for an average of 119.7 psi.

Example Four

Example Four utilizes sand (Wedron 430), Part One, and Part Two of the foundry binder system. Part One includes Bisphenol F epoxy resin (DER 354; lot D344F4G036) at 70% (parts by weight) and cumene hydroperoxide (TRIGONOX K-90) at 30% (parts by weight). Part Two includes epoxy novolac resin (DEN 431; lot D344F79940) at 31% (parts by weight), resorcinol at 3.8% (parts by weight), dibasic ester (DBE) at 7.6%, an acrylate (SR 351H TMPTA) at 56.40% (parts by weight), silane (A187) at 1.2%.

After two minutes from curing at about 30% RH, the three tensile strength test results of the Example Four dog bone sample were 179.5, 157.1, and 150.3, for an average of 162.3 psi. After two hours from curing at about 30% RH, the three tensile strength test results were 202.4, 219.6, and 212.1, for an average of 211.4 psi. After 24 hours from curing at about 30% RH, the three tensile strength test results were 201.4, 236.2, and 231.6, for an average of 223.1 psi. After 24 hours from curing at about 75% RH, the three tensile strength test results were 137.8, 138.1, and 111.8, for an average of 129.2 psi.

Example Five

Example Five utilizes sand (Wedron 520), Part One, and Part Two of the foundry binder system. Part One includes Bisphenol F epoxy resin (Dow DER 354) at 70% (parts by weight) and cumene hydroperoxide (TRIGONOX K-90) at 30% (parts by weight). Part Two includes epoxy novolac resin (DEN 431; lot D344F79940) at 31% (parts by weight), resorcinol at 3.8% (parts by weight), dibasic ester (DBE) at 7.6%, an acrylate (SR 351H TMPTA) at 56.40% (parts by weight), silane (A187) at 1.2%.

After two minutes from curing at about 31% RH, the three tensile strength test results of the Example Five dog bone sample were 213.2, 224.3, and 215.9, for an average of 217.8 psi. After two hours from curing at about 31% RH, the three tensile strength test results were 249.8, 228.7, and 248.3, for an average of 242.3 psi. After 24 hours from curing at about 31% RH, the three tensile strength test results were 276.7, 260.4, and 237.4, for an average of 258.2 psi. After 24 hours from curing at about 75% RH, the three tensile strength test results were 125.5, 124.6, and 120.8, for an average of 123.6 psi.

Example Six

Example Six utilizes sand (Wedron 520), Part One, and Part Two of the foundry binder system. Part One includes Bisphenol F epoxy resin (Dow DER 354) at 70% (parts by weight) and cumene hydroperoxide (TRIGONOX K-90) at 30% (parts by weight). Part Two (a proprietary mix) includes epoxy novolac resin (Dow DEN 431) at 33.85% (parts by weight), resorcinol at 1.9% (parts by weight), dibasic ester (DBE) at 3.8%, an acrylate (SR 351H TMPTA) at 59.25% (parts by weight), silane (A187) at 1.2%.

After two minutes from curing at about 31% RH, the three tensile strength test results of the Example Six dog bone sample were 169.6, 176.6, and 171.6, for an average of 172.6 psi. After two hours from curing at about 31% RH, the three tensile strength test results were 226.6, 225.9, and 208.7, for an average of 220.4 psi. After 24 hours from curing at about 31% RH, the three tensile strength test results were 226.7, 241.9, and 259.7, for an average of 242.8 psi. After 24 hours from curing at about 75% RH, the three tensile strength test results were 113.5, 109.0, and 105.2, for an average of 109.2 psi.

Example Seven

Example Seven utilizes sand (Wedron 520), Part One, and Part Two of the foundry binder system. Part One includes Bisphenol F epoxy resin (Dow DER 354) at 70% (parts by weight) and cumene hydroperoxide (TRIGONOX K-90) at 30% (parts by weight). Part Two (a proprietary mix) includes epoxy novolac resin (Dow DEN 431) at 36.7% (parts by weight), an acrylate (SR 351H TMPTA) at 62.1% (parts by weight), silane (A187) at 1.2%.

After two minutes from curing at about 31% RH, the three tensile strength test results of the Example Seven dog bone sample were 155.9, 178.6, and 173.9, for an average of 169.5 psi. After two hours from curing at about 31% RH, the three tensile strength test results were 210.4, 221.0, and 221.9, for an average of 217.8 psi. After 24 hours from curing at about 31% RH, the three tensile strength test results were 234.2, 213.9, and 205.1, for an average of 217.7 psi. After 24 hours from curing at about 75% RH, the three tensile strength test results were 112.8, 109.7, and 91.6, for an average of 104.7 psi.

Example Eight

Example Eight utilizes sand (Wedron 520), Part One, and Part Two of the foundry binder system. Part One (a proprietary mix) includes Bisphenol F epoxy resin (DER 354) at 69% (parts by weight), Bisphenol A epoxy resin (Dow DER 383) at 1% (parts by weight), and cumene hydroperoxide (TRIGONOX K-90) at 30% (parts by weight). Part Two includes epoxy novolac resin (Dow DEN 431) at 31% (parts by weight), resorcinol at 3.8% (parts by weight), dibasic ester (DBE) at 7.6%, an acrylate (SR 351H TMPTA) at 56.40% (parts by weight), silane (A187) at 1.2%.

After two minutes from curing at about 31% RH, the three tensile strength test results of the Example Nine dog bone sample were 199.1, 203.8, and 203.0, for an average of 202.0 psi. After two hours from curing at about 31% RH, the three tensile strength test results were 224.2, 226.6, and 252.8, for an average of 234.5 psi. After 24 hours from curing at about 31% RH, the three tensile strength test results were 261.5, 228.5, and 244.2, for an average of 244.7 psi. After 24 hours from curing at about 75% RH, the three tensile strength test results were 129.6, 123.4, and 119.3, for an average of 124.1 psi.

Example Nine

Example Nine utilizes sand (Wedron 520), Part One, and Part Two of the foundry binder system. Part One (a proprietary mix) includes Bisphenol F epoxy resin (DER 354) at 68% (parts by weight), Bisphenol A epoxy resin (Dow DER 383) at 2% (parts by weight), and cumene hydroperoxide (TRIGONOX K-90) at 30% (parts by weight). Part Two includes epoxy novolac resin (Dow DEN 431) at 31% (parts by weight), resorcinol at 3.8% (parts by weight), dibasic ester (DBE) at 7.6%, an acrylate (SR 351H TMPTA) at 56.40% (parts by weight), silane (A187) at 1.2%.

After two minutes from curing at about 31% RH, the three tensile strength test results of the Example Nine dog bone sample were 187.8, 200.5, and 195.1, for an average of 194.5 psi. After two hours from curing at about 31% RH, the three tensile strength test results were 238.1, 242.9, and 227.5, for an average of 236.2 psi. After 24 hours from curing at about 31% RH, the three tensile strength test results were 245.2, 221.9, and 250.2, for an average of 239.1 psi. After 24 hours from curing at about 75% RH, the three tensile strength test results were 126.7, 110.1, and 120.1, for an average of 119.0 psi.

Example Ten

Example Ten utilizes sand (Wedron 520), Part One, and Part Two of the foundry binder system. Part One (a proprietary mix) includes Bisphenol F epoxy resin (DER 354) at 69% (parts by weight), Bisphenol A epoxy resin (Dow DER 383) at 1% (parts by weight), and cumene hydroperoxide (TRIGONOX K-90) at 30% (parts by weight). Part Two (a proprietary mix) includes epoxy novolac resin (Dow DEN 431) at 36.7% (parts by weight), an acrylate (SR 351H TMPTA) at 62.1% (parts by weight), silane (A187) at 1.2%.

After two minutes from curing at about 31% RH, the three tensile strength test results of the Example Ten dog bone sample were 173.2, 185.6, and 193.7, for an average of 184.2 psi. After two hours from curing at about 31% RH, the three tensile strength test results were 234.2, 238.9, and 243.7, for an average of 238.9 psi. After 24 hours from curing at about 31% RH, the three tensile strength test results were 262.6, 232.6, and 233.5, for an average of 242.9 psi. After 24 hours from curing at about 75% RH, the three tensile strength test results were 115.6, 116.8, and 104.9, for an average of 112.4 psi.

SUMMARY OF TENSILE STRENGTH EXAMPLES

The foregoing examples demonstrates that blends of epoxy novolac resins and bisphenol-F epoxy resin can be used to make cores with adequate tensile strength. Other experiments indicate that the addition of bisphenol A epoxy resin has does not have a detrimental effect on the tensile strength of the dog bones or foundry cores made with the binder.

Exemplary Shake Out Test

The shake out test for castings has been used extensively to develop no-bake and cold box binders with improved shakeout for aluminum castings in the shakeout test, castings are measured by placing the solidified casting (specific time from pouring to be determined by test program) onto a pneumatic vibrator for a selected time, then the loose sand is removed and the core and retained sand weighed. Cycle is repeated until 100% of the sand is removed by vibration. A secondary benefit is the ability to look at surface finish.

A shakeout test was conducted utilizing a core mold made from sand (Badger FW-55), Part One, and Part Two. Part One was formed from Part One includes Bisphenol F epoxy resin (Dow DER 354) at 70% (parts by weight) and cumene hydroperoxide (TRIGONOX K-90) at 30% (parts by weight). Part Two includes epoxy novolac resin (Dow DEN 431) at 31% (parts by weight), resorcinol at 3.8% (parts by weight), dibasic ester (DBE) at 7.6%, an acrylate (SR 351H TMPTA) at 56.40% (parts by weight), silane (A187) at 1.2%.

Furnace dwell times were measured at six 5-minute intervals (i.e., 5 minutes, 10 minutes, 15 minutes, 20 minutes, 25 minutes, and 30 minutes). The furnace temperature was 800° F. The cooling time for each test interval was 5 minutes.

For the first shakeout test associated with the 5 minute shakeout test dwell time interval, prior to the dwell time, the weight of the crucible/pan was 216.83 g, the combined weight of the crucible/pan with the core sample was 326.05, thus the core sample was 109.22 g. After a dwell time of 5 minutes (and cooling for another 5 minutes), the combined weight of the crucible/pan with the core sample (after burning) was 325.78 g. The difference between the pre-burn combined weight and the post-burn combined weight was 0.27 (326.05−325.78). The post-burn crucible/pan and burned sand weight was 217.64 g. The burned sand less the crucible/pan weight was 0.81 (217.64−216.83). The unburned sand sample weight less the burned sand was 108.41 (109.22−0.81). Thus, the shakeout percentage (% SHAKEOUT) was 0.74% (0.81/109.22×100=0.74%).

For the second shakeout test associated with the 10 minute shakeout test dwell time interval, prior to the dwell time, the weight of the crucible/pan was 217.19 g, the combined weight of the crucible/pan with the core sample was 325.72 g, thus the core sample was 108.53 g. After a dwell time of 10 minutes (and cooling for another 5 minutes), the combined weight of the crucible/pan with the core sample (after burning) was 325.26 g. The difference between the pre-burn combined weight and the post-burn combined weight was 0.46 (325.72–325.26). The post-burn crucible/pan and burned sand weight was 219.26 g. The burned sand less the crucible/pan weight was 2.07 (219.26–217.19). The unburned sand sample weight less the burned sand was 106.46 (108.53–2.07). Thus, the shakeout percentage (% SHAKEOUT) was 1.91% (2.07/108.53×100=1.91%).

For the third shakeout test associated with the 15 minute shakeout test dwell time interval, prior to the dwell time, the weight of the crucible/pan was 215.69 g, the combined weight of the crucible/pan with the core sample was 324.03, thus the core sample was 108.34 g. After a dwell time of 15 minutes (and cooling for another 5 minutes), the combined weight of the crucible/pan with the core sample (after burning) was 323.19 g. The difference between the pre-burn combined weight and the post-burn combined weight was 0.84 (324.03–323.19). The post-burn crucible/pan and burned sand weight was 220.21 g. The burned sand less the crucible/pan weight was 4.52 (220.21–215.69). The unburned sand sample weight less the burned sand was 103.82 (108.34–4.52). Thus, the shakeout percentage (% SHAKEOUT) was 4.17% (4.52/108.34×100=4.17%).

For the fourth shakeout test associated with the 20 minute shakeout test dwell time interval, prior to the dwell time, the weight of the crucible/pan was 215.0 g, the combined weight of the crucible/pan with the core sample was 324.49 g, thus the core sample was 109.49 g. After a dwell time of 20 minutes (and cooling for another 5 minutes), the combined weight of the crucible/pan with the core sample (after burning) was 323.34 g. The difference between the pre-burn combined weight and the post-burn combined weight was 1.15 (324.49–323.34). The post-burn crucible/pan and burned sand weight was 241.69 g. The burned sand less the crucible/pan weight was 26.69 g (241.69–215.0). The unburned sand sample weight less the burned sand was 82.8 g (109.49–26.69). Thus, the shakeout percentage (% SHAKEOUT) was 24.38% (26.69/109.49×100=0.74%).

For the fifth shakeout test associated with the 25 minute shakeout test dwell time interval, prior to the dwell time, the weight of the crucible/pan was 216.30 g, the combined weight of the crucible/pan with the core sample was 325.43, thus the core sample was 109.13 g. After a dwell time of 25 minutes (and cooling for another 5 minutes), the combined weight of the crucible/pan with the core sample (after burning) was 324.14 g. The difference between the pre-burn combined weight and the post-burn combined weight was 1.29 (325.43–24.14). The post-burn crucible/pan and burned sand weight was 282.72 g. The burned sand less the crucible/pan weight was 66.44 (282.72–216.30). The unburned sand sample weight less the burned sand was 42.71 (109.13–66.42). Thus, the shakeout percentage (% SHAKEOUT) was 60.86% (66.42/109.13×100=60.86%).

For the sixth shakeout test associated with the 30 minute shakeout test dwell time interval, prior to the dwell time, the weight of the crucible/pan was 215.31 g, the combined weight of the crucible/pan with the core sample was 324.92, thus the core sample was 109.61 g. After a dwell time of 30 minutes (and cooling for another 5 minutes), the combined weight of the crucible/pan with the core sample (after burning) was 323.5 g. The difference between the pre-burn combined weight and the post-burn combined weight was 1.42 (324.92–323.5). The post-burn crucible/pan and burned sand weight was 323.5 g. The burned sand less the crucible/pan weight was 109.19 (323.5–215.31). The unburned sand sample weight less the burned sand was 1.42 (109.61–109.19). Thus, the shakeout percentage (% SHAKEOUT) was about 100% (109.19/109.61×100=~100%).

Distinctions Over the Prior Art

The foundry binder system of the present disclosure is distinguished from U.S. Pat. No. 6,604,567 inasmuch as no portion of the formulation of the present disclosure (i.e., Part One 102 and Part Two 104; which is commercially known as HyperSET) includes/utilizes an alkyl silicate as required by U.S. Pat. No. 6,604,567. More particularly, the A-187 Silane of the present disclosure is not an alkyl silicate.

The foundry binder system of the present disclosure is distinguished from U.S. Pat. No. 6,662,854 inasmuch as no portion of the formulation of the present disclosure (i.e., Part One 102 and Part Two 104; which is commercially known as HyperSET) includes/utilizes an aliphatic epoxy resin as required by U.S. U.S. Pat. No. 6,662,854. More particularly, the bisphenol-F epoxy resin, bisphenol-A epoxy resin, and novolac resins used in some exemplary formulations discussed above are aromatic resins, not aliphatic resins. As one having ordinary skill in the art recognizes, aliphatic resins are different from aromatic resins.

The foundry binder system of the present disclosure is distinguished from U.S. Pat. No. 6,684,936 inasmuch as no portion of the formulation of the present disclosure (i.e., Part One 102 and Part Two 104; which is commercially known as HyperSET) includes/utilizes a benzylic ether phenolic resole resin as required by U.S. Pat. No. 6,684,936. More particularly, the resorcinol and DBE used in some exemplary formulations discussed above are not benzylic ether phenolic resins.

The foundry binder system of the present disclosure (i.e., Part One 102 and Part Two 104; which is commercially known as HyperSET) is distinguished from U.S. Pat. No. 6,686,402 inasmuch some embodiments use bisphenol A epoxy resin that is specifically excluded through Claim 1 of U.S. Pat. No. 6,686,402.

The foundry binder system of the present disclosure is distinguished from U.S. Pat. No. 7,723,401 inasmuch as no portion of the formulation of the present disclosure (i.e., Part One 102 and Part Two 104; which is commercially known as HyperSET) includes/utilizes an acrylate 5 to 50 parts by weight as required by U.S. Pat. No. 7,723,401. The acrylate used in some exemplary formulations is outside the range provided in U.S. Pat. No. 7,723,401, which causes the foundry binder system of the present disclosure to function and react differently and in an improved manner. Additionally, U.S. Pat. No. 7,723,401 requires 3 to 6 parts by weight of an organofunctional silane. The A-187 Silane in some exemplary formulation is outside the range provided in U.S. Pat. No. 7,723,401, which causes the foundry binder system of the present disclosure to function and react differently and in an improved manner.

Sundry Discussions

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims (if at all), should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures.

An embodiment is an implementation or example of the present disclosure. Reference in the specification to "an embodiment," "one embodiment," "some embodiments," "one particular embodiment," or "other embodiments," or the like, means that a particular feature, structure, or characteristic described in connection with the embodiments is included in at least some embodiments, but not necessarily all embodiments, of the invention. The various appearances "an embodiment," "one embodiment," "some embodiments," "one particular embodiment," or "other embodiments," or the like, are not necessarily all referring to the same embodiments.

If this specification states a component, feature, structure, or characteristic "may", "might", or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

Additionally, any method of performing the present disclosure may occur in a sequence different than those described herein. Accordingly, no sequence of the method should be read as a limitation unless explicitly stated. It is recognizable that performing some of the steps of the method in an different order could achieve a similar result.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of various embodiments of the disclosure are examples and the disclosure is not limited to the exact details shown or described.

What is claimed:

1. A foundry binder system comprising:
a first portion (Part One), wherein Part One includes an epoxy resin in a range from 25 to 70 parts by weight and cumene hydroperoxide in a range from 10 to 40 parts by weight, wherein the epoxy resin of Part One is a Bisphenol F epoxy resin;
a second portion (Part Two), wherein Part Two includes an epoxy novolac resin in a range from 10 to 40 parts by weight, a polyhydroxy benzene in a range from 0.5 to 10 parts by weight, an acrylate in a range from 20 to 70 parts by weight and a dibasic ester in a range of 2 to 10 parts by weight, and wherein the polyhydroxy benzene is one of a resorcinol a non-functionalized resorcinol compound, and a functionalized resorcinol compound.

2. The foundry binder system of claim 1, wherein Part One further comprises Bisphenol A epoxy resin.

3. The foundry binder system of claim 2, wherein the Bisphenol A epoxy resin in Part One is about 1 parts by weight and the Bisphenol F epoxy resin is about 69 parts by weight.

4. The foundry binder system of claim 1, wherein Part Two further includes silane in a range from 0.2 to 5 parts by weight.

5. The foundry system of claim 1, wherein the resorcinol is in a range from 1.5 to 4 parts by weight.

6. The foundry binder system of claim 5, wherein the resorcinol is about 3.8 parts by weight.

7. A foundry mix comprising:
(a) a foundry aggregate;
(b) a binder system, which will cure in the presence of sulfur dioxide and a free radical initiator, the binder system including:
(1) 10 to 70 parts by weight of an epoxy novolac resin;
(2) 0.5 to 10 parts by weight of a polyhydroxy benzene, wherein the polyhydroxy benzene is one of a resorcinol, a non-functionalized resorcinol compound, and a functionalized resorcinol compound;
(3) 20 to 70 parts by weight of a monomeric or polymeric acrylate; and
(4) a free radical initiator, and
(5) 2 to 10 parts by weight of a dibasic ester,
where said parts by weight are based upon 100 parts by weight of the binder system.

8. The foundry mix of claim 7, wherein the binder system further includes at least 1 parts by weight of bisphenol A epoxy resin.

9. The foundry binder system of claim 7, wherein the binder system further includes (6) a silane in a range from 0.2 to 5 parts by weight.

10. The foundry mix of claim 7, wherein the resorcinol is about 3.8 parts by weight.

11. The foundry mix of claim 7, wherein the resorcinol is in a range of 1.5 to 4 parts by weight.

* * * * *